United States Patent [19]

Pevear

[11] Patent Number: 5,288,695

[45] Date of Patent: Feb. 22, 1994

[54] POTASSIUM-ARGON DATING OF ILLITE COMPONENTS IN AN EARTH SAMPLE

[75] Inventor: David R. Pevear, Houston, Tex.

[73] Assignee: Exxon Production Research Company, Houston, Tex.

[21] Appl. No.: 955,951

[22] Filed: Oct. 2, 1992

Related U.S. Application Data

[63] Continuation-in-part of Ser. No. 937,918, Aug. 28, 1992, abandoned.

[51] Int. Cl.$^5$ .................. G01N 33/24; G01N 23/00
[52] U.S. Cl. ............................. 436/27; 436/31; 436/57; 436/58
[58] Field of Search .............. 73/152; 436/27, 57, 436/58, 31

[56] References Cited

U.S. PATENT DOCUMENTS 2,946,657  7/1960  Reynolds .................. 423/119
4,722,220  2/1988  Herron ..................... 73/152

OTHER PUBLICATIONS

Hurley, P. M., Hunt, J. M., Pinson, W. H., and Fairbairn, H. W., 1963, "K-Ar Age Values on the Clay Fractions in Dated Shales," Geochim. et Cosmochim. Acta, v. 27, pp. 279-284.

Hower, J., Hurley, P. M., Pinson, W. H., and Fairbairn, H. W., 1963, "The Dependence of K—Ar Age on the Mineralogy of Various Particle Size Ranges in a Shale," Geochim et Cosmochim Acta, v. 27, pp. 405-410.

Dalrymple, G. B. and Lanphere, M. A., "The Potassium-Argon Clock—How It Works," Potassium-Argon Dating, Chapter 4, pp. 43-51, 1969.

Dalrymple, G. B. and Lanphere, M. A., Potassium-Argon Dating, pp. 177-178, 1969.

Cassignol, C. and Gillot, P. Y., "Range and Effectiveness of Unspiked Potassium-Argon Dating: Experimental Groundwork and Applications", Numerical Dating in Stratigraphy, Part 1, chapter 9, pp. 159-179, 1982.

Pevear, D. R. and Elliott, W. C., "Illite Age Analysis: A Method for Interpreting Shale K/Ar Ages," Abstract for Clay Minerals Society 29th Annual Meeting, Houston, Tex., Oct. 1991.

Mossmann, J. R., Clauer, N., and Liewig, N., "Dating Thermal Anomalies in Sedimentary Basins: The Diagenetic History of Clay Minerals in the Triassic Sandstones of the Paris Basin, France,"0 Clay Minerals (Jun. 1992), v. 27, No. 2, pp. 211-226.

Pevear, D. R., "Illite Age Analysis, a New Tool for Basin Thermal History Analysis," Water-Rock Interaction, Kharaka & Maest (eds) © 1992 Balkema, Rotterdam. ISBN 90 5410 0753, pp. 1251-1254.

Primary Examiner—James C. Housel
Assistant Examiner—Milton I. Cano
Attorney, Agent, or Firm—Gary D. Lawson

[57] ABSTRACT

A process for determining an end member age of an illite component in an earth sample which contains a diagenetic illite component and a detrital illite component. As a first step, the sample is separated into a plurality of fractions so that the fractions will have different mean ages of illite. Next, the relative percentage of one of the illite components is determined for each fraction. The mean age of total illite in each fraction is determined using potassium-argon age analysis. The determined relative percentages are then correlated with the determined mean ages to generate a linear relationship. The end member age for each illite component can then be determined by using the linear relationship since zero percent of one of the illite components corresponds to the end member age of the other illite component.

8 Claims, 1 Drawing Sheet

POTASSIUM-ARGON DATING OF ILLITE COMPONENTS IN AN EARTH SAMPLE

CROSS REFERENCE TO RELATED APPLICATION

This application is a continuation-in-part of the United States patent application Ser. No. 937,918 filed Aug. 28, 1992, now abandoned.

FIELD OF THE INVENTION

This invention relates to geochemistry and more specifically relates to a process for determining the age of illite in an earth sample which contains both detrital illite and diagenetic illite.

BACKGROUND OF THE INVENTION

In the exploration for oil and gas, it is often desirable to determine the age of clay minerals in sedimentary rocks. This information can be used as an aid to determine the genesis, history, and migration pattern of hydrocarbons, fluids, and minerals in sediments. Since sedimentary rocks often contain illite, considerable effort has been made by geologists to determine the date illite was formed in a rock sample.

Various dating techniques have been suggested. A widely used dating technique is known as the potassium(K)-argon(Ar) dating method. This dating technique is based on the principle that when a K-bearing mineral, such as illite, was formed it contained $^{40}K$, one of three isotopes of potassium. The $^{40}K$ then underwent radioactive decay according to a constant decay rate to produce two daughter products, $^{40}Ca$ and $^{40}Ar$. Because Ar is an inert element, it is very unlikely to be taken up into newly formed minerals. Therefore, most if not all argon in a mineral is a result of radioactive decay. The most abundant calcium isotope is $^{40}Ca$, and calcium is more abundant than potassium in the earth's crust. For these reasons, age dating is more reliable using the daughter argon isotope than the daughter calcium isotope even though 89% of all $^{40}K$ decay produces $^{40}Ca$. The amount of $^{40}Ar$ and $^{40}K$ in a sample is determined directly with a mass spectrometer and by inference based on measurement of the total potassium content.

The K-Ar dating technique is relatively simple to use if at the time the earth sample was formed it was not contaminated with previously formed argon. Because argon is an inert gas, it escapes easily from molten rock and begins to accumulate only after the rock solidifies and minerals cool. For this reason the initial argon present in molten rock as it forms is generally not a problem in K-Ar dating. When molten magma was deposited on the earth's surface, any argon that was present in the magma would have been lost to the earth's atmosphere. The magma would have been so hot that the argon gas would have escaped. As the magma cooled it crystallized and trapped potassium ions in the crystalline lattice. The $^{40}K$ began to decay to $^{40}Ar$ and the gaseous $^{40}Ar$ was trapped in the crystal lattice. The age of the sample can be easily determined by comparing the amount of potassium to the amount of argon.

The K-Ar dating technique is more difficult to use if the rock has undergone any chemical alteration or post-formational heating (above about 250° C.). Such heating or chemical alteration may cause some or all of the accumulated argon to escape and thus partially or totally reset the K-Ar clock. Because sedimentary rocks have typically not undergone heating above 250° C., application of K-Ar dating to sedimentary rocks does not suffer from this problem. However, when the K-Ar dating technique was first introduced in the 1950s, it was generally believed the technique was not practical for dating illite found in sedimentary rocks because such rocks contain a mixture of "old" and "new" illite.

As sediments undergo heating during burial, new illite is often formed in the rocks, especially in shales. This newly formed illite is called "diagenetic illite". Since illite is rich in potassium, K-Ar dating can be used to determine when the diagenetic illite was formed. However, the resulting age measured using K-Ar dating can be inaccurate because rocks in which the diagenetic illite forms often also contain old illite which is called "detrital illite". The detrital illite may have been carried there by wind, ocean currents, streams, or rivers millions or hundreds of millions of years before the diagenetic illite was formed.

Because the diagenetic illite formed in response largely to temperature, the amount of it and its age are important indicators of the sediment's thermal history. This information is useful in hydrocarbon exploration because it helps establish the time of maturation of the source rock for oil and gas. Knowing the age of the detrital illite can also help in determining the provenance of the sedimentary rock.

A major difficulty in using the K-Ar dating method on an illite sample that contains both diagenetic illite and detrital illite is determining the relative contribution of each illite component. Since diagenetic and detrital illites were formed at different times, K-Ar dating of the sample would give a mean age of all illite in the sample. Since detrital illite can contain much more argon than the more abundant diagenetic illite, the detrital illite may dominate the age value disproportionately.

Determining sedimentary (diagenetic) age using K-Ar dating is further complicated by the fact that different sized particles in the rock seldom have identical proportions of detrital illite and diagenetic illite. Coarser-sized fractions tend to have K-Ar age values greater than the age of the finer-sized fractions.

Efforts have been made to physically separate diagenetic illite from the detrital illite, but such efforts have not been entirely successful. Even the finer-sized fractions appear to contain mixtures of the two illite components. Therefore, the dates obtained using K-Ar dating are often not useful.

A need exists for an improved process for using the K-Ar dating method to determine the age of detrital illite and the age of diagenetic illite in an earth sample that contains both diagenetic illite and detrital illite.

SUMMARY OF THE INVENTION

This invention relates to a process for determining an end member age of an illite component in an earth sample which contains a diagenetic illite component and a detrital illite component. The first step is to separate the sample into a plurality of fractions, preferably three or more, so that the fractions have varying mean ages of illite. The relative percentage of one of the illite components is then determined for each fraction. The mean age of total illite in each fraction is determined using K-Ar age analysis. A linear relationship between the previously determined relative percentages of illite and the mean ages is calculated, preferably by leastsquares regression analysis. The end member age for either illite component can then be determined by using the linear relationship. Zero percent of one illite component in the sample will correspond to the end member age of the other illite component.

BRIEF DESCRIPTION OF THE DRAWING

The Drawing is a graphical plot showing on the y-axis the age of illite in millions of years determined using K-Ar dating of three fractions of a sample and on the x-axis the percentage of detrital illite of total illite in each fraction.

DESCRIPTION OF THE PREFERRED EMBODIMENT

Figure 1:
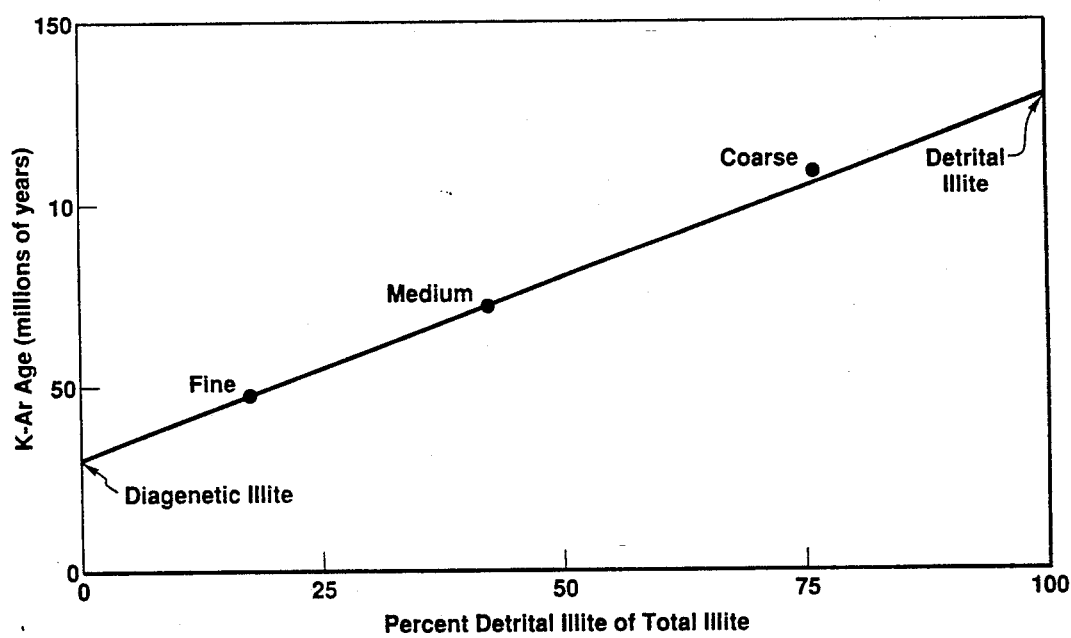

This invention is generally applicable to a process for determining the age of detrital and diagenetic illite in a sample of earth that contains both detrital illite and diagenetic illite. In the practice of this invention a sample of earth containing detrital and diagenetic illite is separated into a plurality of fractions so that the fractions have different mean ages of illite. The percentage of detrital illite in each fraction is then determined using any suitable quantitative analysis technique. Through use of K-Ar dating the mean age of total illite in each fraction is also ascertained. For each fraction, the average age of total illite is correlated with the percentage of detrital illite to develop a linear relationship between the age of total illite and the percentage of detrital illite. Preferably, the linear relationship is determined using least-squares regression analysis. For a preselected percentage of detrital illite, the mean age of illite corresponding to that percentage can then be determined using the linear relationship. The linear relationship can be used to determine the illite age for any detrital percentage from zero percent detrital illite to one hundred percent detrital illite. The age corresponding to zero percent detrital illite is called the "end member" age of diagenetic illite and the age corresponding to one hundred percent detrital illite is called the "end member" age of detrital illite. The practice of this invention effectively determines the end member age of diagenetic illite and the end member age of detrital illite in a sample that contains both detrital and diagenetic components without physically separating the components.

The practice of this invention will be described using a shale sample that contains both diagenetic illite and detrital illite. The amount of sample conventionally used in K-Ar dating methods may be used in the practice of this invention. A 50 gram initial sample is normally sufficient. If the sample is coated with drilling mud or other extraneous materials, it is cleaned using a brush, pick, or other suitable cleaning means.

Before analyzing the rock sample in accordance with the process of this invention, the sample needs to be disaggregated. It is important to take the rock apart into its individual grains without creating any new grains and particularly without creating any new small grains. For this reason the sample is preferably not ground. Disaggregation can be performed using conventional disaggregation techniques. Some samples will fall apart in water. Other samples will fall apart by repeated freezing and thawing. Most rocks disaggregate when subjected to freezing and thawing hundreds of times. Other suitable disaggregation methods may include high-frequency sonic vibration while submerged in a liquid such as water.

The sample may optionally be treated with a buffered acid to remove carbonates to further enhance disaggregation. Acetic acid buffered with sodium acetate may be used for this purpose to bring the pH of the solution to about 5. To further aid disaggregation, following the buffer acid treatment the sample may optionally be treated with hydrogen peroxide to partially dissolve organic matter which may be holding rock particles together. These chemical treatment steps may be interspersed with additional ultrasonic disaggregation.

Next, the aqueous suspension containing the clay particles is separated into a plurality of fractions so that each fraction will have a different mean age of illite. A preferred way of making this separation is to separate the particles by size. Coarser-sized particles tend to contain more detrital illite than finer-sized particles. Therefore, separating the sample into a plurality of fractions with each fraction having different sized particles that fall within a narrow size range will nearly always produce fractions having different mean ages of illite.

One way of separating the sample into a plurality of fractions in accordance with this invention is to subject the aqueous suspension to centrifugation and re-suspension. A minimum of two fractions are required to practice this invention. However, preferably the sample is separated into three or more fractions. Increasing the number of fractions dated in the practice of this invention reduces statistical error. For purposes of clarity and simplicity of presentation, three fractions were separated in this description.

To prepare the first (coarse) fraction, the sample was centrifuged at sufficient speeds and for a time period calculated based on settling rates according to Stokes' law to settle particles larger than about 0.2 microns in diameter and to keep the finer particles (those smaller than 0.2 microns) in suspension. The second (medium) fraction was separated in a similar manner to separate out particles ranging in size between 0.2 microns and 0.02 microns. The third (fine) fraction contained particles smaller than 0.02 microns.

These particle sizes are provided in this description for illustration purposes. Other size distributions for the fractions may be used in the practice of this invention and as mentioned above additional fractions may be made.

A wide size range of particles in each fraction is not desirable because different size particles of the same mineral were commonly formed within the rock sample at different times and they may have different potassium and argon contents. For this reason, a wide range of particle sizes can lead to an inhomogeneous fraction and therefore less difference in age between fractions. The size selected for each fraction can be suitably selected by those skilled in the art, taking into account the natural grain size of illite in the sample and the number of fractions to be analyzed. It has been observed, however, that particles larger than about 2 microns are more likely to contain unwanted minerals such as feldspars.

Other techniques can be used in the practice of this invention to separate the sample into a plurality of fractions having different mean ages of illite. For example, the sample may be passed through an electromagnetic separator which separates iron-rich particles from those particles that are less iron-rich. The procedure generally separates the detrital illite into magnetic and non-magnetic fractions, which have different mean ages of illite.

After the sample has been separated into discrete fractions, the percentage of detrital illite in each fraction is determined. Optionally, the percentage of diagenetic illite may be determined instead of determining the detrital illite or the percentage both illite components may be determined. Any suitable method for making this determination can be used in the practice of this invention. A preferred method calculates the illite percentage using an X-ray diffractometer to obtain an X-ray diffractogram. Data from the X-ray diffractogram is then matched to calculated diffractograms of known samples. This matching is based on the assumption that the detrital illite mineral phase consists of discrete illite particles, whereas diagenetic illite is present as a component of a mixed-layer illite/smectite mineral phase. These two phases can be distinguised from each other on X-ray diffractograms. Calculated diffractograms of the two phases are added to produce a synthetic diffractogram that matches the experimental one. The proportion of discrete illite in the synthetic diffractogram (calculated as weight-percent of total illite) is then taken to represent the amount of detrital illite in the actual earth sample. Preferably, this matching is performed using a suitable computer program. A preferred computer program is called NEWMOD, which is commercially available from Dr. R. C. Reynolds of Dartmouth College in Hanover, N.H. Further information about use of NEWMOD is discussed in *X-Ray Diffraction and the Identification and Analysis of Clay Minerals* by Duane M. Moore and Robert C. Reynolds, Jr., Oxford University Press, 1989.

Another technique for measuring the illite percentage in each fraction is to use a transmission electron microscope (TEM) to determine the chemistry of a representative number of sub-micron size clay particles. Since detrital illite and diagenetic illite have different aluminum/potassium ratios and iron/aluminum ratios, the relative percentage of detrital illite in each fraction can be determined by methods well known to those skilled in the art. This technique is not preferred, however, because it can be time consuming to perform.

Before performing K-Ar dating, each fraction is washed (or dialyzed) and dewatered. The dewatering may be done by freeze drying which produces a fluffy material that can be conveniently handled.

The average age of illite in each fraction is determined using conventional K-Ar dating techniques. The procedures for K-Ar dating are well known to those skilled in the art and do not need further explanation. For reference, see *Potassium-Argon Dating* by G. B. Dalrymple et al., W. H. Freeman and Company, 1969.

Referring to the Drawing, the percentage of detrital illite of the total illite in each fraction that was measured for each sample was plotted on the x-axis and the corresponding average age of illite in millions of years for each fraction was plotted on the y-axis. Although the Drawing plots the percentage of detrital illite on the x-axis, it should be understood that in the practice of this invention the x-axis may alternatively plot the percentage of diagenetic illite of the total illite in each fraction.

For the sample analyzed in this description of the invention, the fraction containing coarse particles (between 2 microns and 0.2 microns in diameter) had a detrital illite percent of 78 and an average illite age of 108 million years. The sample fraction containing medium-sized particles (between 0.2 microns and 0.02 microns) had a detrital illite percent of 43 and an average illite age of 72 million years. The sample fraction containing the fine particles (less than 0.02 microns) had a detrital illite percent of 18 and an average illite age of 48 million years.

The three points plotted in the Drawing for the sample analyzed for purposes of this description were correlated assuming a linear relationship. This correlation is preferably performed using least-squares regression. This is a well-known technique for plotting a best-fit line whenever the data points do not fall exactly on a straight line.

The age of the diagenetic illite in the sample was determined by extrapolating the linear relationship to zero percent detrital illite, which is also referred to as the "diagenetic end member." Referring again to the Drawing, for the sample used in this description the diagenetic end member age was 31 million years. The age of the detrital illite in the sample was similarly determined by extrapolating the straight line to one hundred percent detrital illite, which is also referred to as the "detrital end member age." In this embodiment, the detrital end member age was 128 million years.

The principle of the invention and the best mode in which it is contemplated to apply that principle have been described. For the sake of brevity, a detailed description of equipment used in the practice of this invention has not been made since all of the equipment is well known to those skilled in the art. It is to be understood, however, that the forgoing is illustrative only and that other means and techniques can be used without departing from the true scope of the invention defined in the following claims.

What I claim is:

1. A process for determining an end member age of an illite component in an earth sample which contains a diagenetic illite component and a detrital illite component, comprising the steps of:
   (a) separating the earth sample into a plurality of fractions by a separation means which separates the earth sample into discrete fractions having different sized particles;
   (b) determining for each fraction the relative percentage of one of the illite components;
   (c) determining through potassium-argon age analysis the mean age of total illite in each fraction;
   (d) correlating the relative percentages determined in step (b) with the mean ages determined in step (c) to generate a linear relationship; and
   (e) determining an end member age for said one of the illite components using said linear relationship, whereby zero percent of said one of the illite components corresponds to the end member age of the other illite component.

2. The process of claim 1 in which the relative percentage of one of said illite components is determined in step (b) for detrital illite.

3. The process of claim 1 wherein the earth sample is separated into three fractions wherein said fractions have different mean ages of illite.

4. The process of claim 3 wherein the diameter of particles in one fraction range between 2.0 microns and 0.2 microns, the diameter of particles in the second fraction range between 0.2 microns and 0.02 microns, and the diameter of particles in the third fraction are less than 0.02 microns.

5. The process of claim 1 wherein the relative percentage of each illite component is determined using X-ray diffraction analysis.

6. The process of claim 1 wherein the linear relationship is determined using least-squares regression analysis.

7. A process for determining the age of diagenetic illite in an earth sample which contains both detrital and diagenetic illite, comprising the steps of:
   (a) separating the earth sample into a plurality of fractions by a separation means which separates the earth sample into discrete fractions having different sized particles so that each fraction will have a different mean age of illite;
   (b) determining through X-ray diffraction analysis the relative percentage of detrital illite in each fraction;
   (c) determining through potassium-argon age analysis the mean age of total illite in each fraction;
   (d) determining a linear relationship based on changes of the relative percentages determined in step (b) compared to changes in the mean ages determined in step (c); and
   (e) determining the age of diagenetic illite by linearly extrapolating said linear relationship to zero percent detrital illite.

8. A process for determining the age of detrital illite in an earth sample which contains both detrital and diagenetic illite, comprising the steps of:
   (a) separating the earth sample into a plurality of fractions by a separation means which separates the earth sample into discrete fractions having different sized particles, each fraction having particles of illite within a narrow size range;
   (b) determining through X-ray diffraction analysis the relative percentage of detrital illite in each fraction;
   (c) determining through potassium-argon age analysis the mean age of total illite in each fraction;
   (d) correlating said relative percentages and said mean ages to determine a linear relationship between said mean ages and said relative percentages in each fraction; and
   (e) determining the age of detrital illite by linearly extrapolating said linear relationship to one hundred percent detrital illite.

* * * * *